(12) United States Patent
Bylsma

(10) Patent No.: US 11,752,231 B2
(45) Date of Patent: Sep. 12, 2023

(54) SCENT DISPERSAL DEVICE

(71) Applicant: Todd Alan Bylsma, Martinsville, IN (US)

(72) Inventor: Todd Alan Bylsma, Martinsville, IN (US)

( * ) Notice: Subject to any disclaimer, the term of this patent is extended or adjusted under 35 U.S.C. 154(b) by 73 days.

(21) Appl. No.: 17/449,846

(22) Filed: Oct. 4, 2021

(65) Prior Publication Data
US 2023/0109004 A1 Apr. 6, 2023

(51) Int. Cl.
A61L 9/12 (2006.01)
A01M 29/12 (2011.01)
A01M 31/00 (2006.01)

(52) U.S. Cl.
CPC .............. A61L 9/122 (2013.01); A01M 29/12 (2013.01); A01M 31/008 (2013.01); A61L 2209/15 (2013.01)

(58) Field of Classification Search
None
See application file for complete search history.

(56) References Cited

U.S. PATENT DOCUMENTS

| | | | |
|---|---|---|---|
| 4,548,764 A | 10/1985 | Munteanu et al. | |
| 5,368,866 A | 11/1994 | Loucas | |
| 5,379,545 A | 1/1995 | Gall et al. | |
| 5,638,977 A * | 6/1997 | Bianchi | B65D 55/06 292/259 R |
| 5,729,928 A * | 3/1998 | Anderson | A01K 97/02 43/44.99 |
| 6,442,887 B2 * | 9/2002 | Sanquist | A01K 97/05 43/56 |
| 6,635,266 B2 | 10/2003 | Messina | |
| 6,923,977 B1 | 8/2005 | Boyce | |
| 7,687,084 B2 | 3/2010 | Tien et al. | |
| 9,198,435 B2 | 12/2015 | Bailey-Jackson | |
| 9,572,348 B2 | 2/2017 | Messina | |
| 9,693,566 B2 | 7/2017 | Messina, Sr. | |
| 10,398,130 B2 | 9/2019 | Birch et al. | |
| 2004/0050950 A1 * | 3/2004 | Brown | A01M 1/2055 239/57 |
| 2004/0168363 A1 | 9/2004 | Baker | |
| 2004/0244722 A1 | 12/2004 | Scharenberg et al. | |
| 2009/0130053 A1 | 5/2009 | Weiser | |
| 2009/0152380 A1 | 6/2009 | Houseknecht et al. | |
| 2009/0255164 A1 * | 10/2009 | Jones | A01K 97/02 43/4.5 |
| 2009/0260271 A1 | 10/2009 | Bailey | |
| 2017/0071195 A1 | 3/2017 | Dussich, Jr. et al. | |
| 2017/0099843 A1 | 4/2017 | Kerk | |

(Continued)

OTHER PUBLICATIONS

Allied-Thermoformed Plastic Products for Construction. Allied Plastics LLC. pp.1-3. https://alliedplastics.com/industries/construction/#:~:text=Thermoformed%20Plastics.,bring%20to%20the%20Construction%20industry. (Year: 2016).*

(Continued)

Primary Examiner — Jelitza M Perez
(74) Attorney, Agent, or Firm — Dunlap Bennett & Ludwig, PLLC; Anna L. Kinney

(57) ABSTRACT

A scent dispersal device includes a cylindrical container and a weatherproof cap that couples to the cylindrical container. The container has a closed end, an open end, and a diameter. The cap has a diameter greater than the container diameter.

4 Claims, 4 Drawing Sheets

(56) References Cited

U.S. PATENT DOCUMENTS

2017/0118996 A1    5/2017  Messina et al.
2019/0297870 A1*  10/2019  Johnson ................ A01M 29/12
2019/0336637 A1*  11/2019  Webster ................. A61L 9/042

OTHER PUBLICATIONS

Watson—What is PVC? Watson & Wolfe, pp.1-3. https://www.watsonwolfe.com/2021/02/25/what-is-pvc/#:~:text=Yes%2C%20PVC%20is%20a%20plastic,waterproof%2C%20and%20weather%20resistant%20materials. (Year: 2021).*
Adreco-Polypropylene Pastic Uses. Adreco Plastics, pp.1-4. https://adrecoplastics.co.uk/polypropylene-uses/ (Year: NA).*

* cited by examiner

SCENT DISPERSAL DEVICE

CROSS-REFERENCE TO RELATED APPLICATION

N/A

BACKGROUND OF THE INVENTION

The present invention relates to garden pest repellents and game attractants and, more particularly, to an scent dispersal device.

Gardeners are plagued by animals digging and eating plants in gardens as well as potted plants. Existing commercially available repellents have toxins, sonic noise, or flashing strobes impacting nearby neighbors and pets. Sonic devices and strobe lights may be activated by wind and blowing leaves. They generally require solar power which requires sunshine or battery power and/or have proprietary and expensive refills. Battery devices do not last in inclement weather. The toxins in chemical repellents impact necessary insects for garden and flower health.

As can be seen, there is a need for a non-toxic, inexpensive repellent device that does not require power.

SUMMARY OF THE INVENTION

In one aspect of the present invention, a scent dispersal device is provided, comprising a cylindrical container having a first closed end, a second open end, and a first diameter; and a weatherproof cap having a second diameter greater than the first diameter, wherein the weatherproof cap is operative to couple to the cylindrical container.

These and other features, aspects and advantages of the present invention will become better understood with reference to the following drawings, description, and claims.

DETAILED DESCRIPTION OF THE INVENTION

Figure 1:
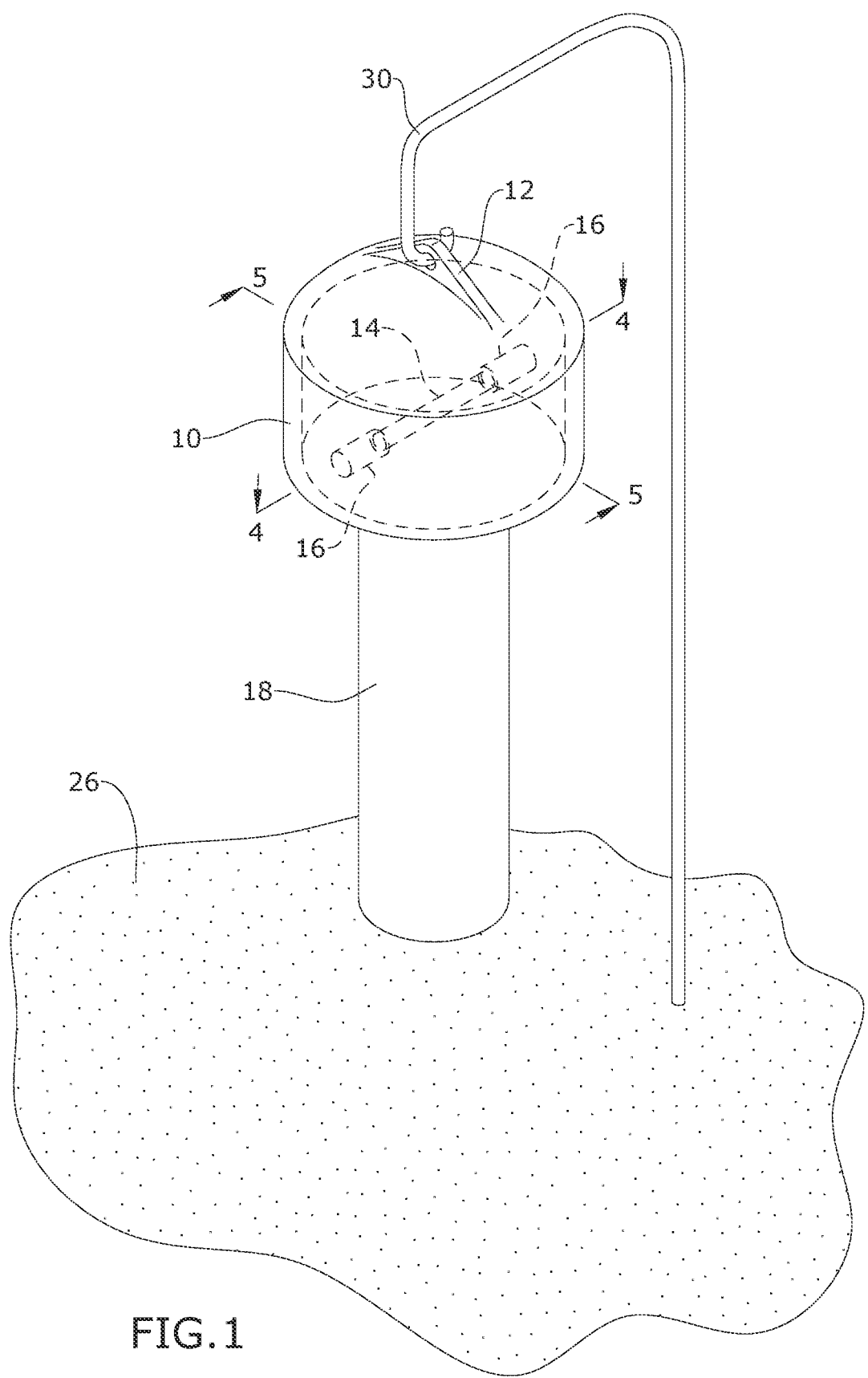
FIG. 1 is a perspective view of a scent dispersal device according to an embodiment of the present invention.

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

Broadly, one embodiment of the present invention is a scent dispersal device comprising a liquid container suspended from a cap such that a consistent space or gap remains between the liquid container and the cap around their circumferences. The inventive device is a durable, weatherproof simple solution that is easy to install and refill. No moving parts, expensive refills or power are required.

The inventive device may use all-natural vinegar as a repellent. As the vinegar is exposed to the air, this odor comes out from under the top cover and continuously settles to the ground. Problem garden animals detest the smell of vinegar and will actively move to avoid smelling it. The device leverages animals' sense of smell and is generally undetectable by humans unless they are positioned low to the ground and within a few feet. The device used with vinegar may be effective over a 10×10 ft. area to keep away rabbits, chipmunks, raccoons, deer, dogs, cats, and squirrels.

Alternatively, the device may be utilized to attract game animals by filling the reservoir with commercial game attractants. The device provides a better method of dispersion when hunting.

In some embodiments, a small solar powered fan may be used to increase dispersion, although the fan may increase the detection of the scent by humans.

To use the dispersal device, a user may establish an open-air location for installation of device, which may be suspended from, for example, a shepherds' staff, tree branch, or fence post. The device may be hung by the top cap connector so that it hangs in a vertical position. The user may grasp the top cap and reservoir and push and turn to separate. Once the reservoir is filled with vinegar or attractant, the user may align the bracket with the opening in reservoir and push and turn to lock.

Once the lift and turn lid is properly attached, there is no need to check the amount of liquid more frequently than once a month and add more vinegar to top off the reservoir. In some cases, after rain and strong storms the device may be refilled.

The device may be manufactured by any known method. The materials of manufacture are not particularly limited. The reservoir and top cap are configured to provide specific coverage and spacing. Once the cap has been formed, a bracket or tabs may be added to the top cap interior and a static hook or connection may be added to the top exterior on the top cap. Once the reservoir has been formed, a J-slot may be cut into the sides of the mouth of the reservoir to provide a push and turn function.

Referring to FIGS. 1 through 7, FIG. 1 illustrates a scent dispersal device according to an embodiment of the present invention comprising a reservoir tube 18, closed on a first end and open on a second end. The reservoir tube 18 is installed onto a weatherproof cap 10 which is suspended above the earth 26 by an exemplary rod hanger 30 inserted through a top cap hanger connector 12 which may be held in place with a bracket or tabs. The cap 10 is weatherproof in that it serves to prevent dilution of the repellent or attractant contents by rain or snow and in that sunlight, precipitation, and extreme temperatures do not functionally degrade the cap.

Figure 2:
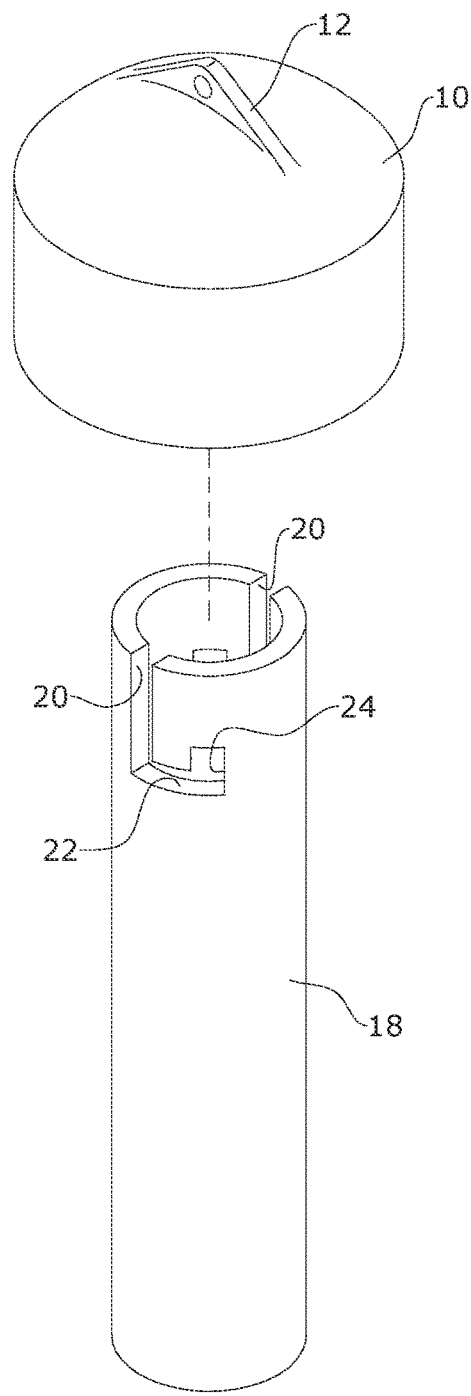
FIG. 2 is an exploded view thereof.
Figure 3:
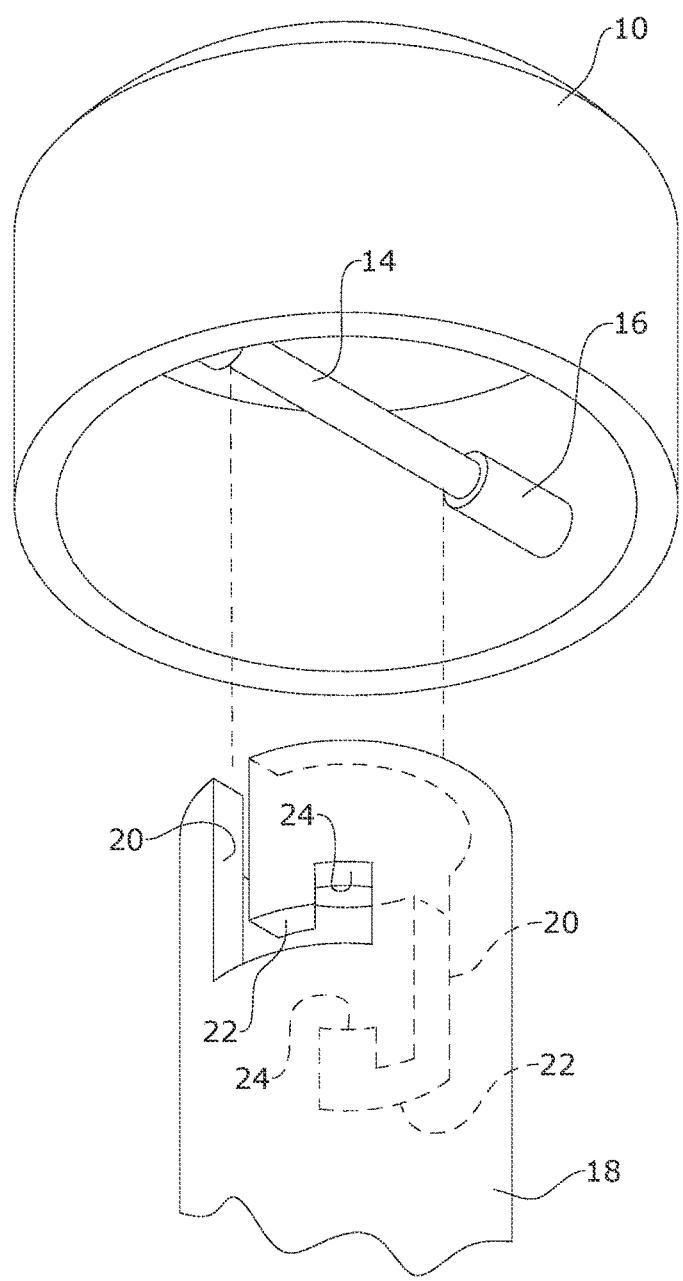
FIG. 3 is a detail exploded view thereof.
Figure 4:
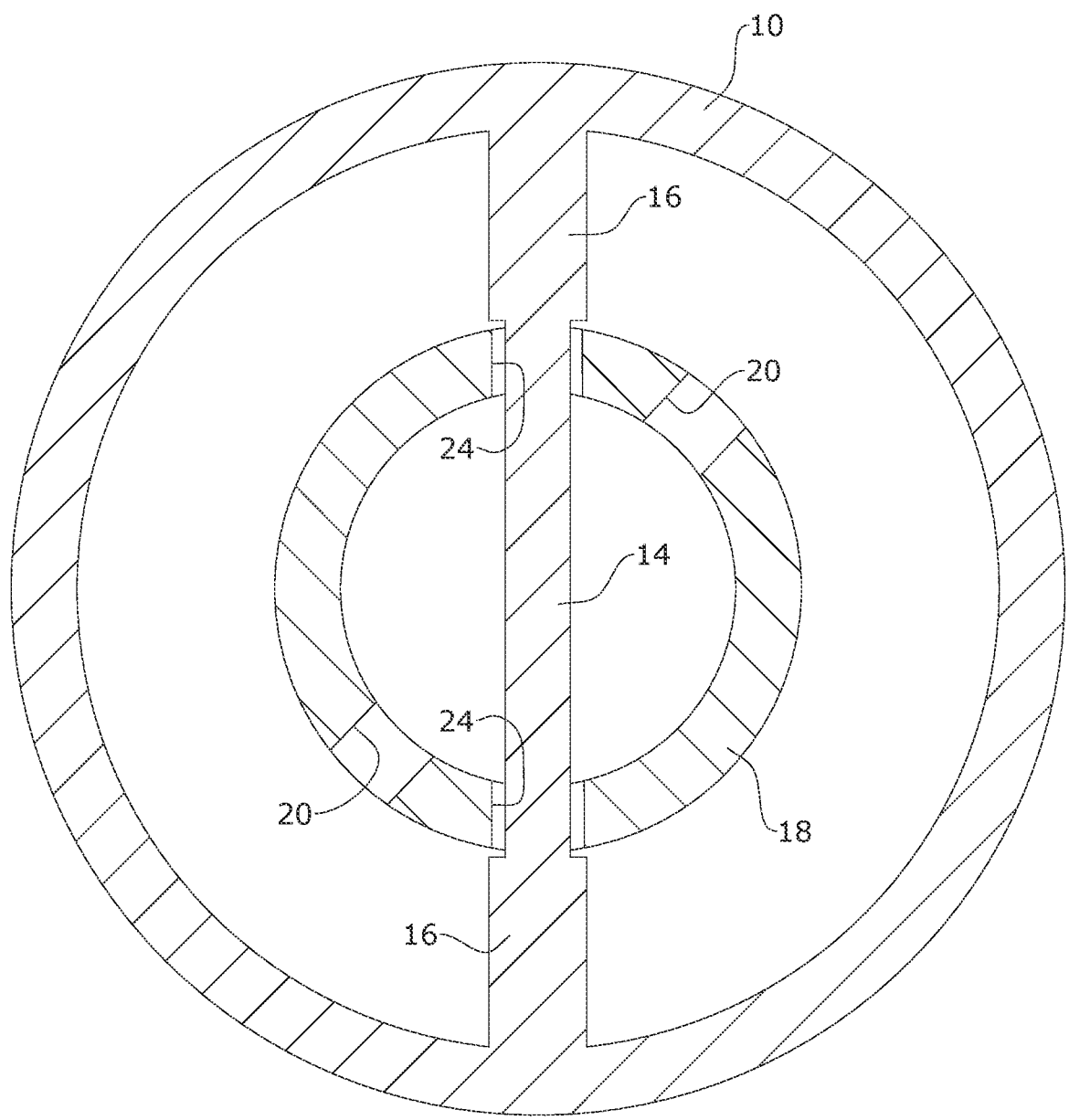
FIG. 4 is a sectional view taken along line 4-4 on FIG. 1.

FIG. 2 more clearly shows the configuration of a pair of opposite J-slots formed in a circumference of the open second end of the reservoir 18, including parallel vertical slots 20 extending from the open end to opposing horizontal slots 22, ending in short vertical slots 24 extending toward the open second end. These J-slots interlock as illustrated in FIG. 4 with a tube mounting rod 14 horizontally suspended in the cap 10 by top cap spacers 16 best shown in FIG. 3. The spacers 16 provide consistent spacing between sides of the cap 10 and the reservoir tube 18.

Figure 5:
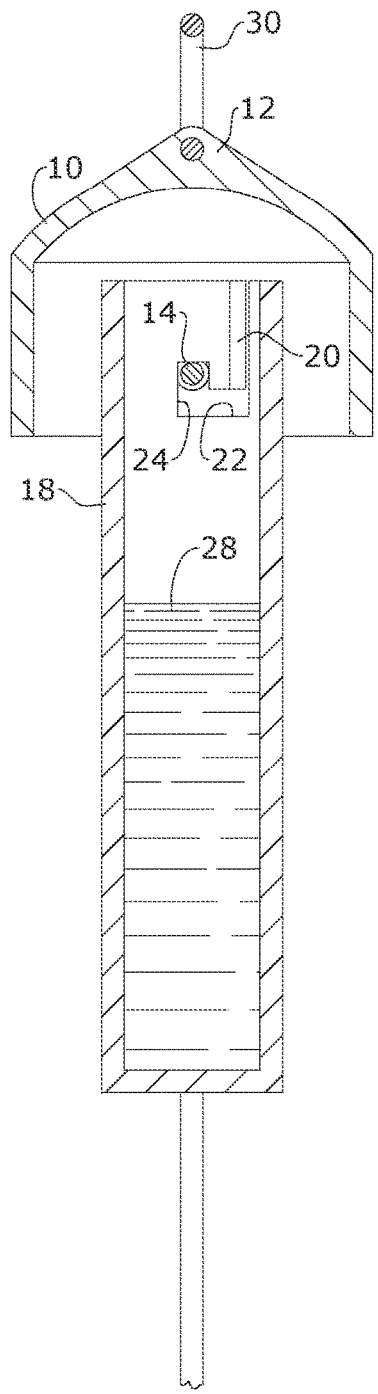
FIG. 5 is a sectional view taken along line 5-5 on FIG. 1.
Figure 6:
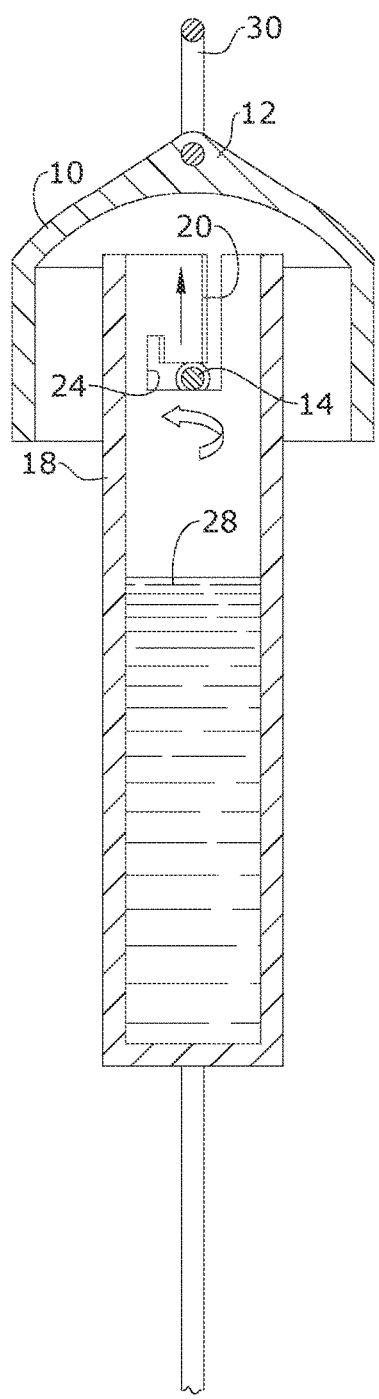
FIG. 6 is a sectional view taken along line 5-5 on FIG. 1, showing motion of the tube.
Figure 7:
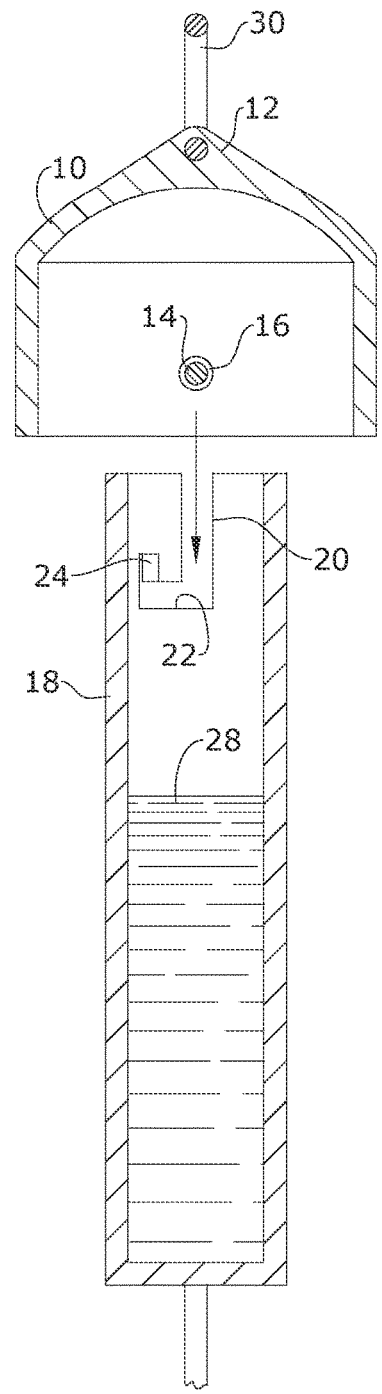
FIG. 7 is a sectional view taken along line 5-5 on FIG. 1, showing removal of the tube.

FIG. 5 illustrates the dispersal device in use position, with the reservoir tube 18 containing liquid 28 such as vinegar repellent, while FIGS. 6 and 7 show removal of the reservoir tube 18 from the cap 10, including the lift-and-twist motion illustrated in FIG. 6.

It should be understood, of course, that the foregoing relates to exemplary embodiments of the invention and that modifications may be made without departing from the spirit and scope of the invention as set forth in the following claims.

What is claimed is:

1. A scent dispersal device comprising:
   a) a cylindrical container having a closed first end, an open second end, and a first diameter; and
   b) a weatherproof cap having a second diameter greater than the first diameter, wherein the weatherproof cap is operative to removably couple to the cylindrical container such that the cylindrical container is suspended from the weatherproof cap;
   wherein the weatherproof cap further comprises a horizontal mounting rod on an internal surface; and
   wherein the cylindrical container has a pair of opposite J-slots formed in a circumference of the open second end, wherein the J-slots are operative to interlock with the horizontal mounting rod.

2. The scent dispersal device of claim 1, further comprising a solar powered fan operative to move air across the open second end of the cylindrical container.

3. The scent dispersal device of claim 1, wherein the weatherproof cap further comprises a suspension connector on an exterior surface.

4. The scent dispersal device of claim 1, wherein each of the J-slots comprises a vertical slot extending from the second open end to a horizontal slot, a distal end of the horizontal slot having a second vertical slot extending toward the open second end.

* * * * *